United States Patent
Baynham (10) Patent No.: US 12,185,987 B2
(45) Date of Patent: Jan. 7, 2025

(54) BONE ANCHOR BASED RETRACTOR/DISTRACTOR

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 311 days.

(21) Appl. No.: 17/492,353

(22) Filed: Oct. 1, 2021

(65) Prior Publication Data

US 2022/0104854 A1 Apr. 7, 2022

Related U.S. Application Data

(60) Provisional application No. 63/086,822, filed on Oct. 2, 2020.

(51) Int. Cl.
*A61B 17/70* (2006.01)
*A61B 17/68* (2006.01)

(52) U.S. Cl.
CPC ...... *A61B 17/7053* (2013.01); *A61B 17/7035* (2013.01); *A61B 17/7076* (2013.01); *A61B 2017/681* (2013.01)

(58) Field of Classification Search
CPC . A61B 17/02; A61B 17/0206; A61B 17/0218; A61B 17/025; A61B 2017/0256
See application file for complete search history.

(56) References Cited

U.S. PATENT DOCUMENTS

| | | | |
|---|---|---|---|
| 8,636,655 B1 * | 1/2014 | Childs | A61B 17/0206 600/219 |
| 9,795,370 B2 * | 10/2017 | O'Connell | A61B 17/0218 |
| 9,924,859 B2 * | 3/2018 | Lee | A61B 5/24 |
| 10,945,773 B2 * | 3/2021 | Medeiros | A61B 17/025 |
| RE48,534 E * | 4/2021 | Bowman | A61B 17/025 |
| 2007/0073111 A1 * | 3/2007 | Bass | A61B 17/0206 600/219 |
| 2007/0100212 A1 * | 5/2007 | Pimenta | A61B 17/848 600/210 |
| 2009/0131755 A1 * | 5/2009 | White | A61B 17/02 606/279 |
| 2011/0130793 A1 * | 6/2011 | Woolley | A61B 17/7076 606/279 |
| 2011/0224497 A1 * | 9/2011 | Weiman | A61B 17/02 600/231 |

(Continued)

*Primary Examiner* — Ellen C Hammond
(74) *Attorney, Agent, or Firm* — McHale & Slavin, P.A.

(57) ABSTRACT

A bone anchor based retractor/distractor assembly for simultaneous tissue retraction and disc space distraction utilizing an adjustable, flexible wire to secure the bone anchors during the distraction process. The assembly includes first and second modular retractor/distractor blades that can be detached for securing to the bone anchor. Each blade has a pivot pin and blade connector with a rotatable knob for adjusting of a wire releasably securable to a bone anchor. The blade connectors are attached to the first and second arm elements, each having a stabilizing arm that is movable in relation to each other by a threaded draw rod having an adjustment knob for activating movement. A main body is secured to a medial retraction blade by an arm having a gear member operatively associated with a gear knob for incremental movement of the medial retraction blade.

17 Claims, 10 Drawing Sheets

(56) References Cited

U.S. PATENT DOCUMENTS

| | | | |
|---|---|---|---|
| 2012/0232350 A1* | 9/2012 | Seex | A61B 17/02 |
| | | | 600/206 |
| 2012/0296171 A1* | 11/2012 | Lovell | A61B 17/025 |
| | | | 600/213 |
| 2019/0110785 A1* | 4/2019 | Serokosz | A61B 17/0206 |
| 2019/0216453 A1* | 7/2019 | Predick | A61B 17/7077 |
| 2021/0186477 A1* | 6/2021 | Buehlmann | A61B 17/025 |
| 2021/0228379 A1* | 7/2021 | Abdou | A61F 2/4455 |
| 2021/0401423 A1* | 12/2021 | Eckhof | A61B 17/7077 |
| 2023/0270428 A1* | 8/2023 | Douglas | A61F 2/4455 |
| | | | 600/201 |

* cited by examiner

BONE ANCHOR BASED RETRACTOR/DISTRACTOR

PRIORITY CLAIM

In accordance with 37 C.F.R. § 1.76, a claim of priority is included in an Application Data Sheet filed concurrently herewith. Accordingly, the present invention claims priority to U.S. Provisional Patent Application No. 63/086,822 entitled "BONE ANCHOR BASED RETRACTOR/DIS-TRACTOR", filed Oct. 2, 2020. The content of the above referenced application is incorporated herein by reference in its entirety.

FIELD OF THE INVENTION

This invention is related to the field of spinal surgery and, more specifically, to a simultaneous tissue retraction and disc space distraction utilizing an adjustable, flexible wire to secure the bone anchors during the distraction process.

BACKGROUND OF THE INVENTION

Surgical approach for addressing spinal injuries and pathologies commonly involves implanting various devices for correcting the spine, including intervertebral stabilization, distraction, decompression, joint fusion, or combinations thereof. Bone screws are most commonly used for anchoring of plates, rods, and tethers used in various combinations to achieve desired correction to the spine. Conventionally, there are three modes of access to the spine for achieving delivery of spinal correction devices. These general modes include anterior through the abdominal cavity), posterior (including transforaminal), and lateral. Modes of access for achieving fusion between lumbar vertebrae; anterior access known as "ALIF" (Anterior Lumbar Interbody Fusion); posterior access known as "PLIF" (Posterior Lumbar Interbody Fusion); and minimally invasive posterior access known as "TLIF".

It is preferable, when operating on the spine, to employ the least invasive surgical approach possible for achieving correction to minimize trauma, associated pain and blood loss experienced by the patient, to improve recovery time and outcomes, and to reduce operating room time and costs. In all modes of approach, one or more special retractors and tubes are typically used to dissect and displace tissue and expose the vertebrae, and other instruments are used to release the annulus.

There is a need for a surgical approach and associated instrumentation and devices that avoid the existing complications known in the art with the various modes of spinal access. More specifically, there is a need for advances with instrumentation and surgical technique to allow for the more desirable prone patient positioning during spinal access surgery, combined with the benefits of lateral access to the target intervertebral space.

SUMMARY OF THE INVENTION

Disclosed is an assembly for simultaneous tissue retraction and disc space distraction utilizing an adjustable, flexible wire to secure the bone anchors during the distraction process. The bone anchor based retractor/distractor assembly is formed from a first modular retractor/distractor blade having a pivot pin and blade connector with a rotatable knob for adjusting of a wire releasably securable to a first bone anchor, and a second modular retractor/distractor blade having a pivot pin and blade connector with a rotatable knob for adjusting of a wire releasably securable to a second bone anchor. Each blade connector is secured to an arm having a release mechanism. The release mechanism allows each of attachment to a bone anchor. The blade connectors are attached to the first and second arm elements, each having a stabilizing arm that is movable in relation to each other by a threaded draw rod having an adjustment knob for activating movement. A main body is secured to a medial retraction blade by an arm having a gear member operatively associated with a gear knob for incremental movement of the medial retraction blade. A cross bar support bridges the left and right stabilizing arms without limiting the pivoting between the arms. Wires incorporated with each blade are used to engage the bone anchors.

An objective of the invention is to provide a direct visualization retractor/distractor assembly adapted for stable engagement with the spine.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DETAILED DESCRIPTION OF THE INVENTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 1:
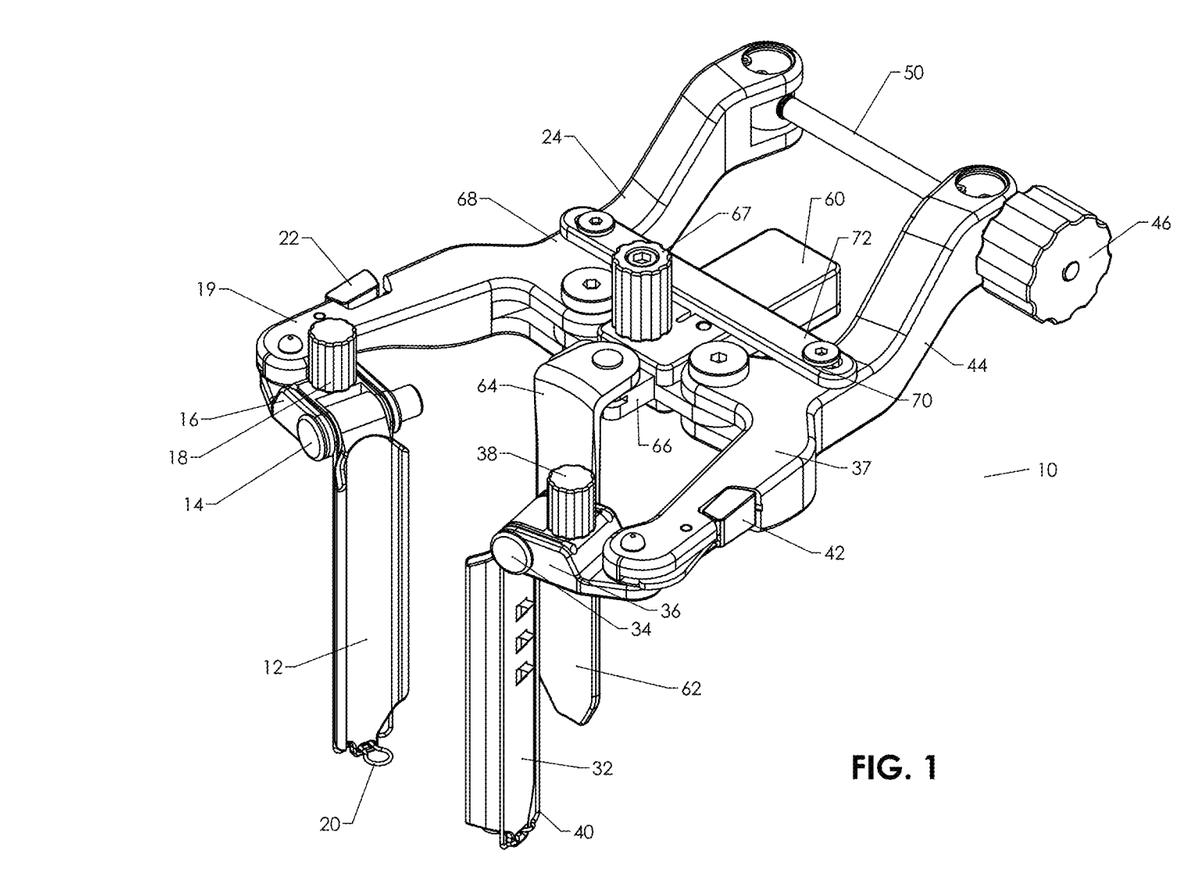
FIG. 1 is a perspective view of the bone anchor based retractor/distractor.

Referring now to FIG. 1, illustrated is a bone anchor based retractor/distractor assembly 10 formed from a first modular retractor/distractor blade 12 secured by a first pivot pin 14 and first blade connector 16 having a rotatable knob 18 for adjusting of a wire 20. The first blade connector 16 is releasably secured to a left arm 19 using a release button 22. The left arm 19 extends to a left stabilizing arm 24.

A second modular retractor/distractor blade 32 is secured by a second pivot pin 34 and second blade connector 36 having a rotatable knob 38 for adjusting of wire 40, The second blade connector 36 is releasably secured to a right arm 37 using a release button 42. The right arm 37 extends to a right stabilizing arm 44. The left stabilizing arm 24 is movable in relation to the right stabilizing arm 44 by a threaded draw rod 50 for drawing the two arms 24, 44 together by use of an adjustment knob 46 for activating the threaded draw rod 50.

A main body 60 is secured to a medial retraction blade 62 by a medial retraction arm 64 with a gear member 66 operatively associated with a gear knob 67 for actively moving the medial retraction blade 62. The left arm 19 is pivotally coupled to the main body 60 by a first pivot pin 68; the right arm 37 is pivotally coupled to the main body 60 by a second pivot pin 70. A cross bar support 72 bridges the left and right stabilizing arm 24, 44.

Figure 2:
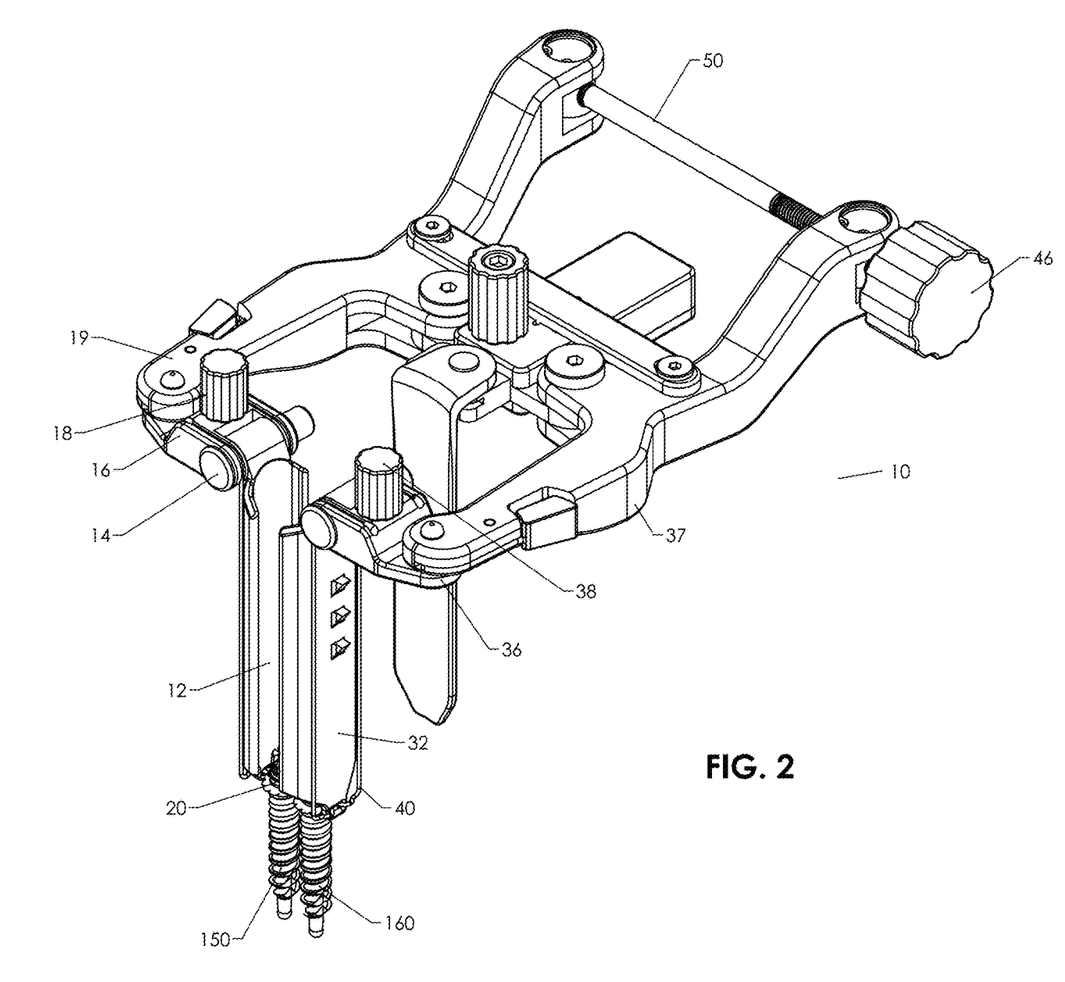
FIG. 2 is a perspective view of the bone anchor based retractor/distractor with bone anchors attached.

FIG. 2 depicts a bone anchor 150 secured to the first blade 12 by wire 20, the wire being adjusted by knob 18. Similarly, bone anchor 160 is secured to the second blade 32 by wire 40, which is adjusted by knob 38. The spacing of blade 12 and blade 32 are spaced apart by threaded draw rod 50, which is rotated by adjustment knob 46.

Figure 3:
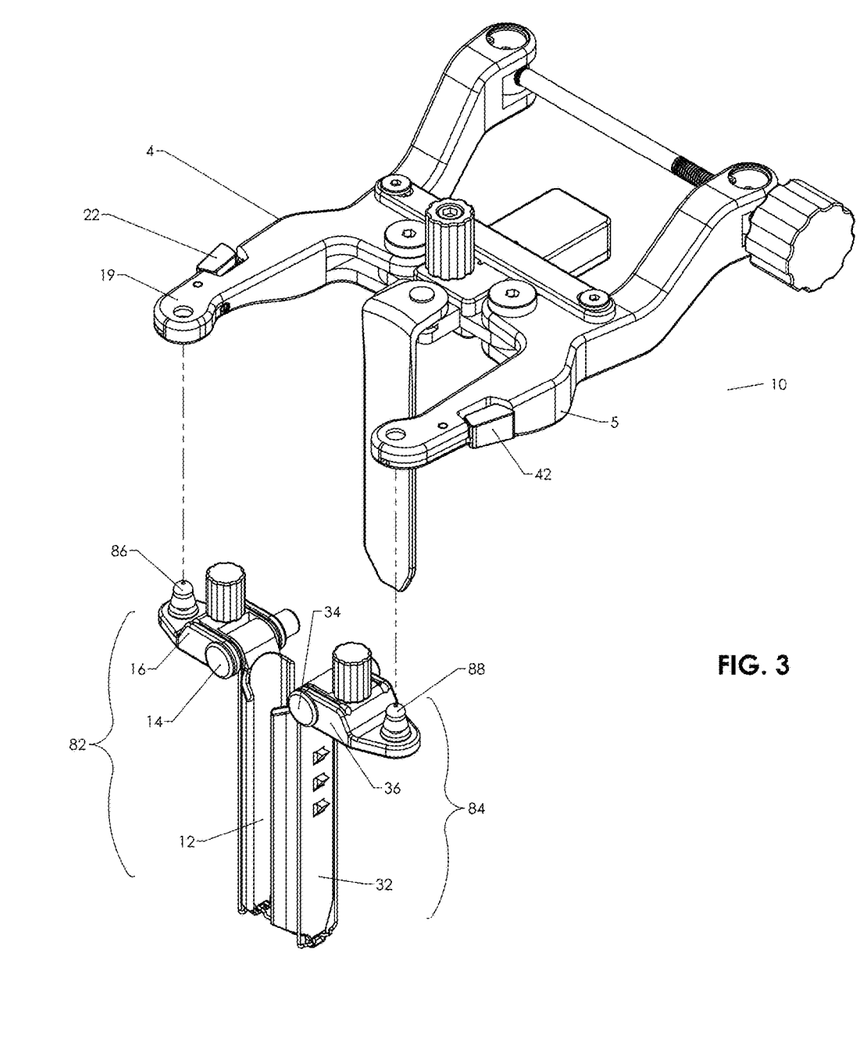
FIG. 3 is a perspective view of the bone anchor based retractor/distractor with the blade assemblies detached.

FIG. 3 is a perspective view of the retractor/distractor assembly 10 with blade assembly 82 and blade assembly 84 detached. Blade assembly 82 is depicted with blade 12 coupled to the first blade connector 16 by first pivot pin 14; the first blade connector having an attachment pin 86 that is releasably secured to the left arm 19. The attachment pin 86 is constructed and arranged to be released from the left arm 19 by the release button 22. Blade assembly 84 is depicted with blade 32 coupled to the second blade connector 36 by second pivot pin 38; the second blade connector having attachment pin 88 that is releasably secured to the right arm 37. The attachment pin 88 is constructed and arranged to be released from the right arm 37 by the release button 42.

Figure 4:
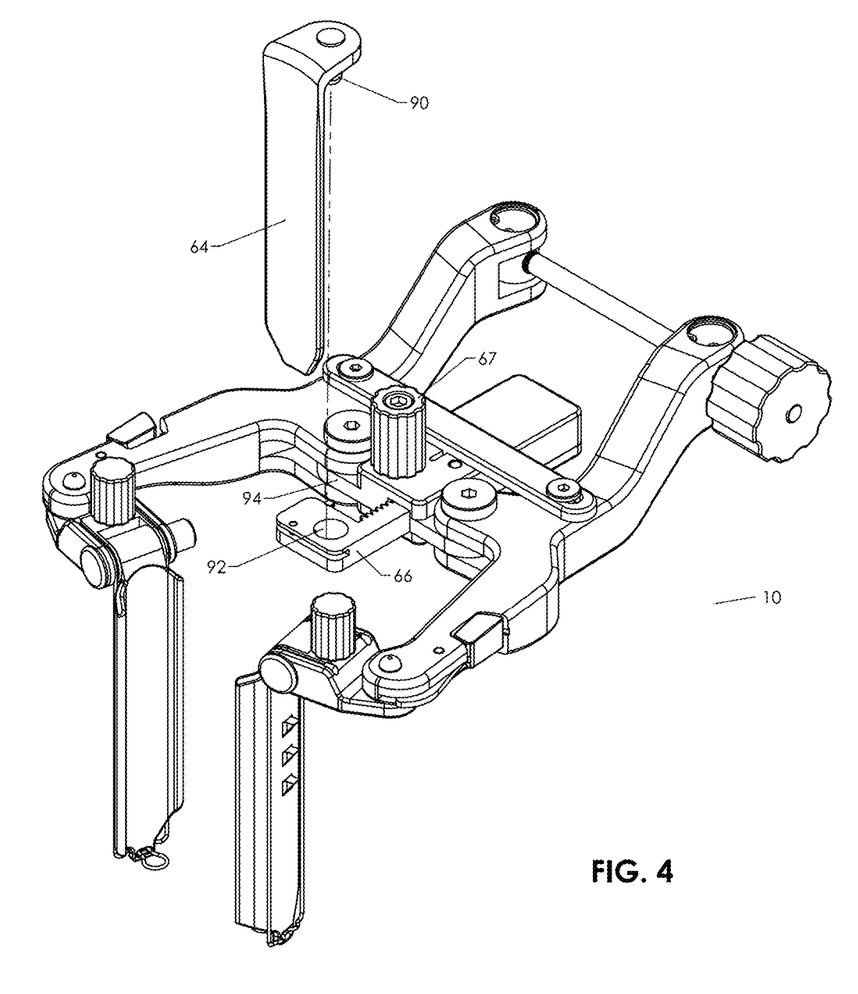
FIG. 4 is a perspective view of the bone anchor based retractor/distractor with the medial retraction blade detached.

FIG. 4 is an exploded view depicting the medial retraction arm 64 having a connector pin 90 removed from the gear member 66 having an aperture 92; the gear member 66 having teeth 94 operatively associated with the gear knob 67. Rotation of the gear knob 67 moves the gear member 66 in an expanded and retracted position.

Figure 5:
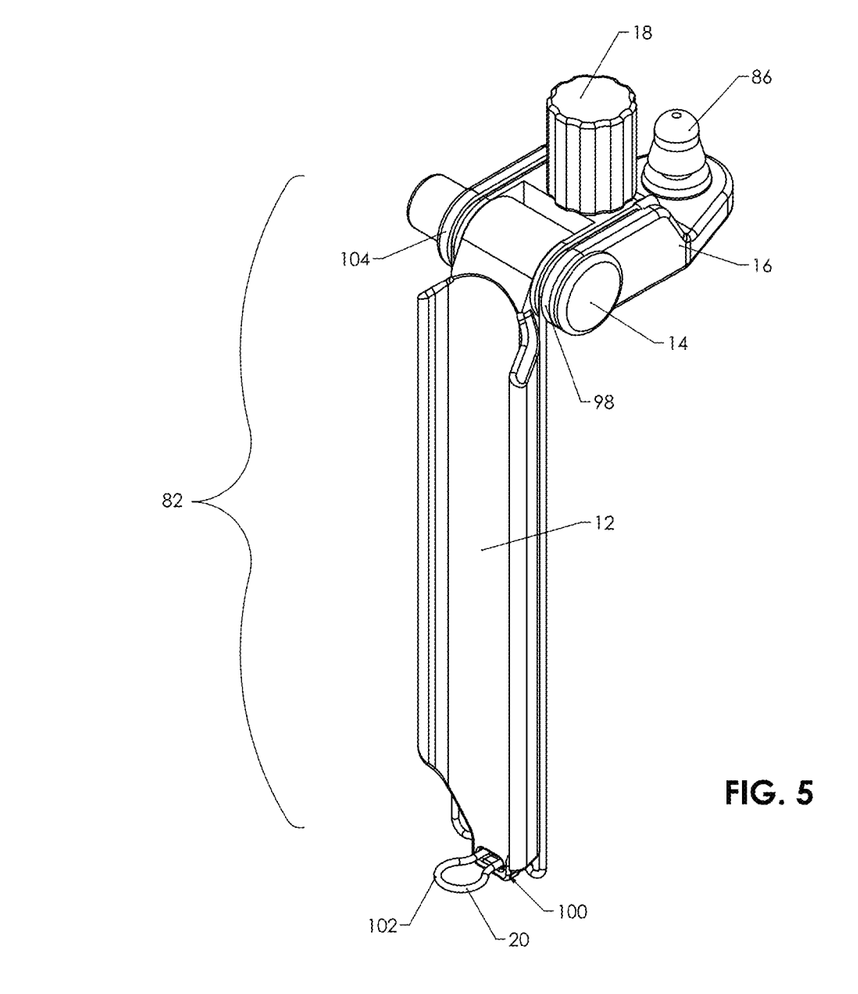
FIG. 5 is a perspective view of a blade connector.
Figure 6:
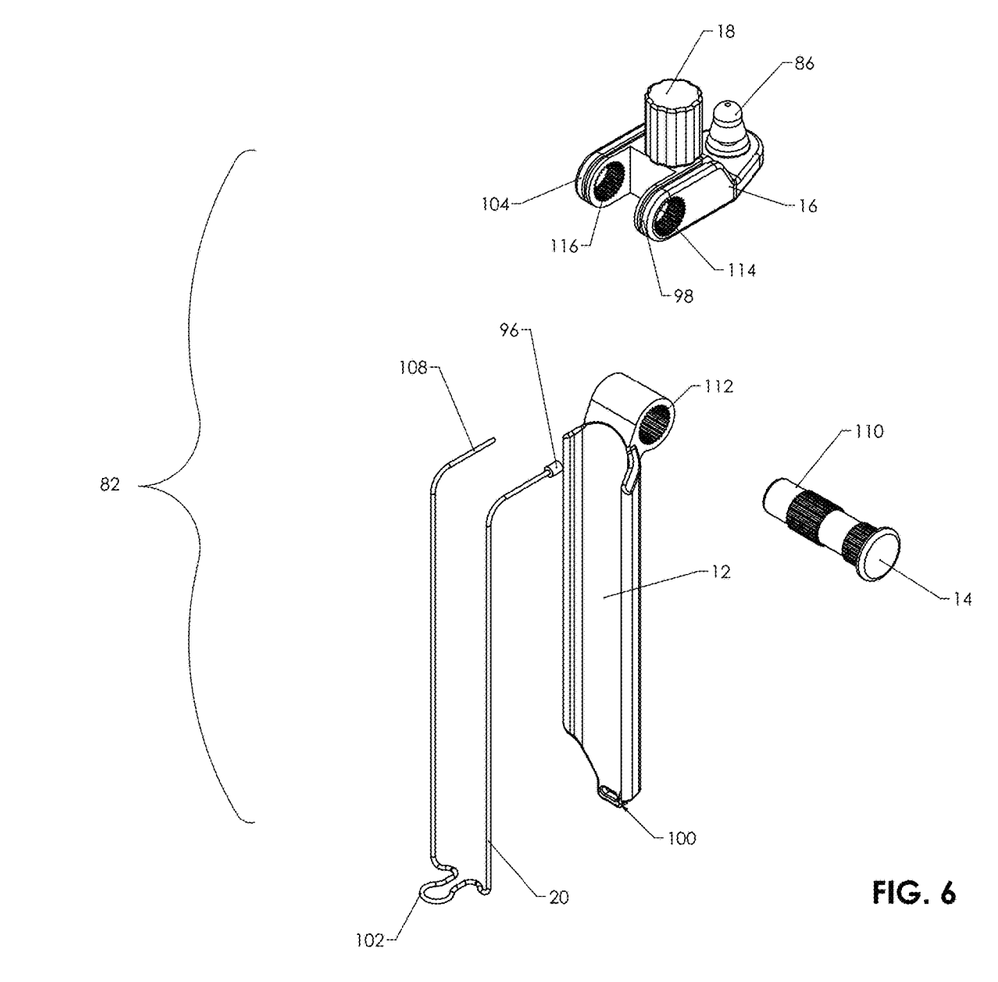
FIG. 6 is an exploded view of the blade connector.

FIGS. 5 and 6 illustrates the blade assembly 82 comprising the blade 12 coupled to the first blade connector 16 by first pivot pin 14. The first blade connector having an attachment pin 86. Wire 20 has a first end 96 that extends along a pathway 98 through aperture 100 to form an expandable hoop 102 upwards through pathway 104 with a second end 108 secured to knob 18. The knob 18 is used to expand or contract the size of the hoop 102 used to engage the top of a bone anchor. The pivot pin 14 includes a gnarled finished 110 constructed and arranged to cooperate with an interfacing finish 112 of blade opening 113, and first blade connector 16 apertures 114 and 116. Movement of the pivot pin 14 allows angular positioning of the blade 12.

Figure 7:
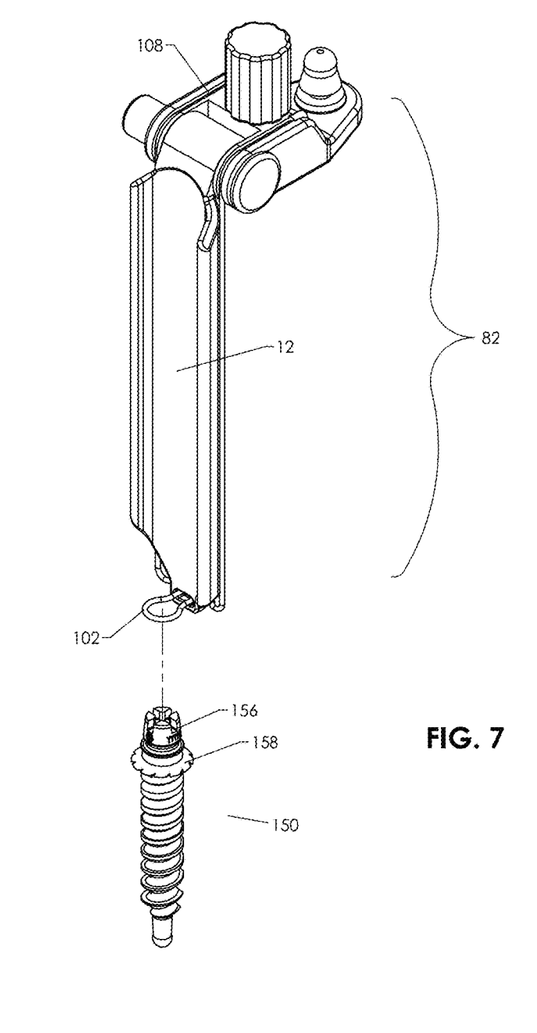
FIG. 7 is a perspective view of the blade connector with a detached bone anchor.
Figure 8:
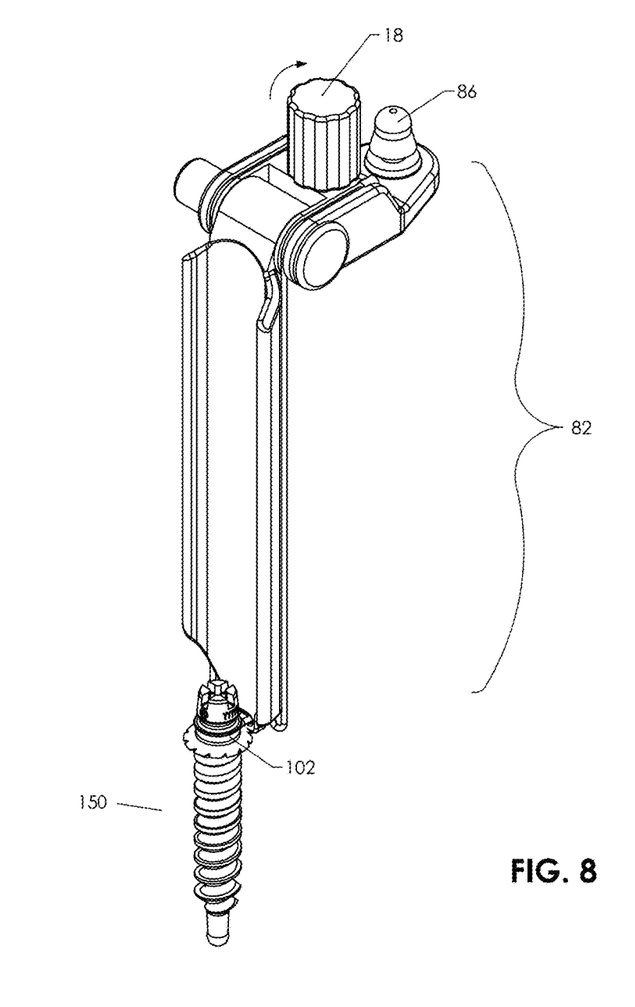
FIG. 8 is a perspective view of the blade connector with an attached bone anchor.

FIG. 7 illustrates the blade assembly 82 being attached to a bone anchor 150; the bone anchor having a top section 156 with a rib 158, wherein the hoop 102 engages the rib 158. As illustrated in FIG. 8, the knob 18 is rotated to contract the loop 102 by drawing the end of the wire 108 through pathway 104. With the bone anchor 150 attached to the blade 12, the blade assembly 82 can be reattached to the left arm 19 by attachment pin 86.

Figure 9:
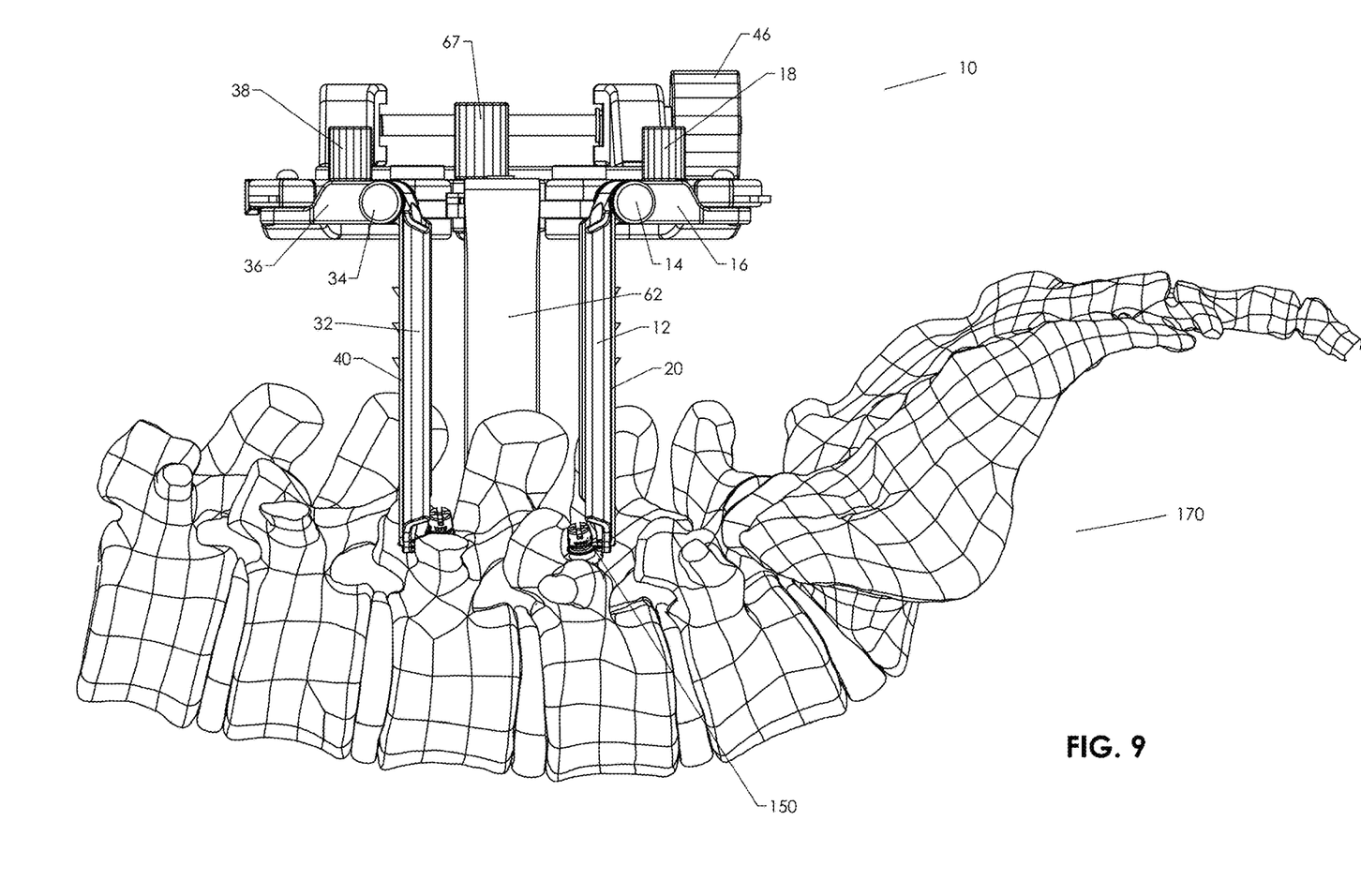
FIG. 9 is a lateral view depicting the bone anchor based retractor/distractor positioned over a spine.
Figure 10:
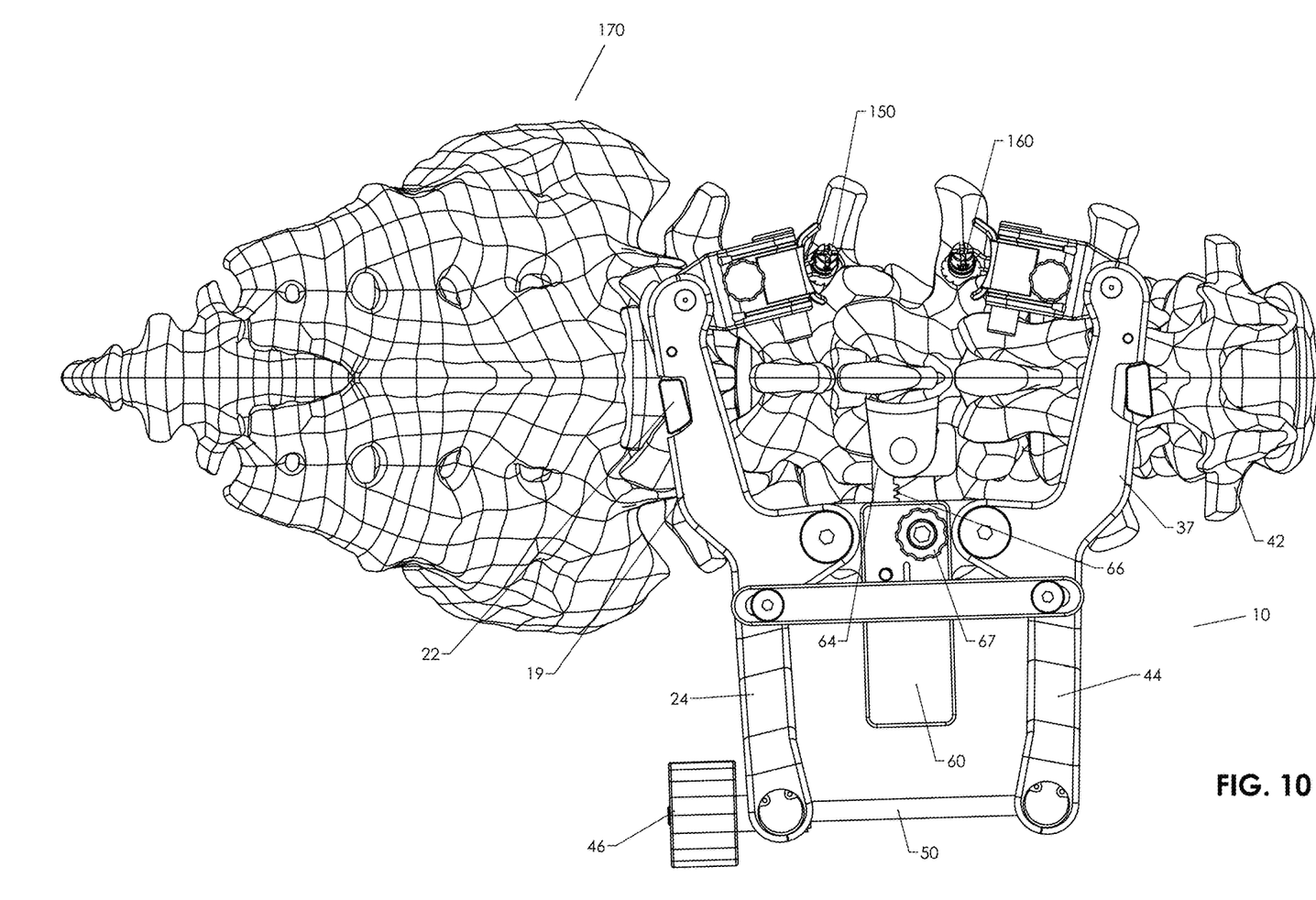
FIG. 10 is a posterior view of FIG. 9.

FIGS. 9 and 10 depict the bone anchor based retractor/distractor 10 positioned over a spine 170. The first modular retractor/distractor blade 12 is secured by a first pivot pin 14 and first blade connector 16 having a rotatable knob 18 for adjusting of a wire 20 that engages a bone anchor 150. The first blade connector 16 is releasably secured to the left arm 19 using a release button 22. The left arm 19 extends to a left stabilizing arm 24. The second modular retractor/distractor blade 32 is secured by a second pivot pin 34 and second blade connector 36 having a rotatable knob 38 for adjusting of a wire 40 that engages a bone anchor 160. The second blade connector 36 is releasably secured to a right arm 37 using a release button 42. The right arm 37 extends to a right stabilizing arm 44. The left stabilizing arm 24 is movable in relation to the right stabilizing arm 44 by a threaded draw rod 50 for drawing the two arms 24, 44 together by use of an adjustment knob 46 for activating the threaded draw rod 50. The main body 60 is secured to a medial retraction blade 62 by a medial retraction arm 64 with a gear member 66 operatively associated with gear knob 67 for actively moving the medial retraction blade 62.

The term "coupled" is defined as connected, although not necessarily directly, and not necessarily mechanically. The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A retractor/distractor assembly comprising:
a main body having a first and second pivot point;
a one-piece left stabilizing arm pivotably coupled to said first pivot point, said left stabilizing arm having a proximate end spaced apart from a distal end;
a first blade having a first attachment pin constructed and arranged to be coupled to an upper end blade opening on said left stabilizing arm spaced apart from a lower end aperture forming a pathway therebetween extending along each side of said first blade, said upper end blade opening releasably secured to said proximate end of said left stabilizing arm;
a first wire having a first end that extends along said first blade pathway forming through said lower end aperture, wherein said hoop is expandable in diameter for releasably securing a bone screw;
a one-piece right stabilizing arm pivotably coupled to said second pivot point, said right stabilizing arm having a proximate end spaced apart from a distal end;
a second blade having a second attachment pin constructed and arranged to be coupled to an upper end blade opening on said right stabilizing arm spaced apart from a lower end aperture forming a pathway therebetween extending along each side of said second blade, said upper end blade opening releasably secured to said proximate end of said right stabilizing arm;
a second wire having a first end that extends along said second blade pathway forming a hoop through said lower end aperture, wherein said hoop is expandable in diameter for releasably securing a bone screw; and
a rod coupled to said distal end of said left stabilizing arm and said right stabilizing arm wherein said rod allows for spacing adjustment of said first distal end of said stabilizing arm about said first and second pivot points located on said main body with reciprocal spacing adjustment of said first and second blade.

2. The retractor/distractor assembly according to claim 1 wherein a first blade connector is releasably secured to said left stabilizing arm, and a second blade connector is releasably secured to said right stabilizing arm.

3. The retractor/distractor assembly according to claim 1 including a first rotatable knob constructed and arranged to adjust the hoop diameter in said first wire.

4. The retractor/distractor assembly according to claim 1 wherein said left stabilizing arm is coupled to a said first blade with a first pin member and said right stabilizing arm is coupled to said second blade with a second pin member.

5. The retractor/distractor assembly according to claim 1 wherein said rod is threaded having a first end rotatably secured to said distal end of said right stabilizing arm and a second end rotatably secured to said distal end of said left stabilizing arm.

6. The retractor/distractor assembly according to claim 5 including an adjustment knob for rotating said threaded rod, wherein rotation of said adjustment knob expands or contracts the spacing between the first and second blade.

7. The retractor/distractor assembly according to claim 1 including a first rotatable knob constructed and arranged to adjust the hoop in said first wire and a second rotatable knob constructed and arranged to adjust the hoop in said second wire.

8. The retractor/distractor assembly according to claim 1 including a retraction blade secured to said main body at a position between said first and second blade.

9. The retractor/distractor assembly according to claim 1 wherein said first blade is releasably secured to said left stabilizing arm.

10. The retractor/distractor assembly according to claim 1 wherein said second blade is releasably secured to said right stabilizing arm.

11. The retractor/distractor assembly according to claim 1 including a cross bar support coupling said left stabilizing arm to said right stabilizing arm.

12. A retractor/distractor assembly comprising:
a main body having a first and second pivot point;
a one-piece left stabilizing arm pivotably coupled to said first pivot point, said left stabilizing arm having a proximate end spaced apart from a distal end;
a first blade having a first attachment pin constructed and arranged to be coupled to an upper end blade opening on said left stabilizing arm spaced apart from a lower end aperture forming a pathway therebetween extending along each side of said first blade, said upper end blade opening coupled to said proximate end of said left stabilizing arm;
a first wire having a first end that extends along said first blade pathway forming a hoop through said lower end aperture, wherein said hoop is expandable in diameter for releasably securing a bone screw;
a one-piece right stabilizing arm pivotably coupled to said second pivot point, said right stabilizing arm having a proximate end spaced apart from a distal end;
a second blade having a second attachment pin constructed and arranged to be coupled to an upper end blade opening on said right stabilizing arm spaced apart from a lower end aperture forming a pathway therebetween extending along each side of said second blade, said upper end blade opening coupled to said proximate end of said right stabilizing arm;
a second wire having a first end that extends along said second blade pathway forming a hoop through said lower end aperture, wherein said hoop is expandable in diameter for releasably securing a bone screw;
a retraction blade secured to said main body at position between said first and second blade; and
a rod coupled to said distal end of said left stabilizing arm and said right stabilizing arm, said rod is threaded having a first end rotatably secured to said distal end of said right stabilizing arm and a second end rotatably secured to said distal end of said left stabilizing arm;
wherein said rod allows for spacing adjustment of said first distal end of said stabilizing arm about said first and second pivot points located on said main body with reciprocal spacing adjustment of said first and second blade.

13. The retractor/distractor assembly according to claim 12 including a first rotatable knob constructed and arranged to adjust the hoop in said first wire.

14. The retractor/distractor assembly according to claim 12 wherein each said stabilizing arm is coupled to a blade with a pin member.

15. The retractor/distractor assembly according to claim 12 including an adjustment knob for rotating said threaded rod, wherein rotation of said adjustment knob expands or contracts the spacing between the first and second blade.

16. The retractor/distractor according to claim 12 including a first rotatable knob constructed and arranged to adjust the hoop in said first wire and a second rotatable knob constructed and arranged to adjust the hoop in said second wire.

17. The retractor/distractor assembly according to claim 12 including a cross bar support coupling said left stabilizing arm to said right stabilizing arm.

* * * * *